United States Patent [19]

Markle et al.

[11] Patent Number: 4,889,407
[45] Date of Patent: Dec. 26, 1989

[54] OPTICAL WAVEGUIDE SENSOR AND METHOD OF MAKING SAME

[75] Inventors: David R. Markle, Paoli, Pa.; Barry C. Crane, Aston Clinton; Michael P. Irvine, London, both of England

[73] Assignee: Biomedical Sensors Limited, High Wycombe, England

[21] Appl. No.: 279,384

[22] Filed: Dec. 2, 1988

[51] Int. Cl.$^4$ .......................... G02B 6/02; A61B 5/00; B23K 9/00; G01N 33/48

[52] U.S. Cl. ........................ 350/96.29; 350/96.10; 350/96.30; 350/96.34; 350/320; 128/634; 219/121.6; 219/121.71; 250/227; 250/230; 356/39

[58] Field of Search ............... 350/96.10, 96.15, 96.29, 350/96.30, 96.32, 96.34, 320; 128/633, 634; 219/121.6, 121.61, 121.7, 121.71; 356/39, 432, 402; 250/227, 230, 231 R; 526/329.7

[56] References Cited

U.S. PATENT DOCUMENTS

| | | | |
|---|---|---|---|
| Re. 31,879 | 5/1985 | Lübbers et al. | 128/633 X |
| 4,200,110 | 4/1980 | Peterson et al. | 128/634 |
| 4,344,438 | 8/1982 | Schultz | 128/634 |
| 4,476,870 | 10/1984 | Peterson et al. | 128/634 |
| 4,560,248 | 12/1985 | Cramp et al. | 350/96.34 |
| 4,600,310 | 7/1986 | Cramp et al. | 350/96.29 |
| 4,710,623 | 12/1987 | Lipson et al. | 250/227 |
| 4,785,814 | 11/1988 | Kane | 128/634 |
| 4,794,619 | 12/1988 | Tregay | 350/96.29 X |
| 4,796,633 | 1/1989 | Zwirkoski | 128/634 |
| 4,801,187 | 1/1989 | Elbert et al. | 350/96.15 |
| 4,803,049 | 2/1989 | Hirschfeld et al. | 128/633 X |
| 4,816,130 | 3/1989 | Karakelle et al. | 128/634 X |

FOREIGN PATENT DOCUMENTS

| | | | |
|---|---|---|---|
| 54-155856 | 12/1979 | Japan | 350/96.32 X |
| WO88/04415 | 6/1988 | PCT Int'l Appl. | 350/96.29 X |

*Primary Examiner*—William L. Sikes
*Assistant Examiner*—Brian M. Healy
*Attorney, Agent, or Firm*—Peter C. Richardson; Lawrence C. Akers; Mark Dryer

[57] ABSTRACT

An optical waveguide sensor for determining an analyte in a medium, which sensor comprises an optical waveguide having a portion to be brought into contact with said medium, said portion having a plurality of cells arranged in an array which substantially covers the cross-sectional area of the waveguide, each of said cells containing an indicator sensitive to said analyte, and a method for the preparation of said sensor.

22 Claims, 1 Drawing Sheet

OPTICAL WAVEGUIDE SENSOR AND METHOD OF MAKING SAME

BACKGROUND OF THE INVENTION

The invention relates to an optical waveguide sensor, particularly an optical fiber sensor and more particularly a sensor formed from an optical fiber having a particular unique configuration wherein a suitable indicator is retained within preformed cells in the optical fiber. More particularly, the invention is concerned with a sensor machined out of a single fiber and to a method for the preparation of such sensor.

Optical fiber (or fiber optic) chemical sensors or probes are well known in the art and such sensors normally comprise an optical fiber in association with a suitable indicator for the analyte under investigation. The indicator may be bound to the fiber by chemical or physical means or may be enveloped by a suitable membrane which is permeable to the analyte.

U.S. Pat. No. 4,200,110 discloses a fiber optic probe which includes an ion permeable membrane envelope which encloses the ends of a pair of optical fibers. The probe operates on the technique of optically detecting a change in the color of a pH sensitive dye.

U.S. Reissue Pat. No. 31,879 discloses a method for measuring the concentration of an analyte in a sample which involves measuring a change in the color characteristic of a fluorescent indicator attached to an optical fiber, without or with a gas-permeable membrane.

In each of the above systems the indicator is attached to the end of the fiber optic probe by chemical bonding or with the aid of a diffusion membrane.

It has now been found that certain difficulties previously encountered in the production of an absorption indicator-containing fiber optic sensor can be avoided by retaining the absorption indicator in pre-formed holes in the optical fiber. The same technique also may be used for other types of indicators, for example fluorescent and luminescent indicators.

Furthermore, the technique is applicable to optical waveguides other than optical fibers; for example, integrated optic chips.

SUMMARY OF THE INVENTION

In accordance with the invention there is provided an optical waveguide sensor for determining an analyte in a medium, which sensor comprises an optical waveguide having a portion to be brought into contact with said medium, said portion having a plurality of cells arranged in an array which substantially covers the cross-sectional area of the waveguide, each of said cells containing an indicator sensitive to said analyte.

As used herein the term "cell" is intended to mean a space which has been formed in the waveguide and into which an indicator may be placed. Said space may be of any shape; is defined by a wall or walls within the waveguide and has at least one opening in a wall through which the indicator may be introduced.

The term "indicator" is intended to mean an entity which undergoes a detectable change or provides a detectable signal in the presence of an analyte. Thus, it may include, but is not restricted to, any one of the following:

(i) a compound which changes color in the presence of an analyte, i.e. a chromogenic indicator;
(ii) a substance which absorbs light of a particular wavelength to produce an absorption signal, the intensity of which changes in the presence of an analyte, i.e. an absorption indicator;
(iii) a substance which fluoresces or luminesces when excited by light of a particular wavelength to provide a fluorescent or luminescent emission whose intensity changes in the presence of analyte, i.e. a fluorescent or luminescent indicator;
(iv) a substance whose refractive index changes when it is subjected to a change in temperature or pressure; i.e. a temperature-sensitive or pressure-sensitive indicator.

In a preferred embodiment, the waveguide is an optical fiber and each of the cells is formed by ablation of a hole in the optical fiber. Preferably the holes are ablated by a high energy laser, for example, an excimer laser.

The invention also provides a method for the preparation of an optical waveguide sensor for determining an analyte in a medium, which comprises selecting a portion of an optical waveguide, subjecting said portion to means for forming one or more cells within the waveguide, immersing said portion in a medium containing an indicator sensitive to said analyte and evacuating said one or more cells until each of said cells is filled with said indicator.

DETAILED DESCRIPTION OF THE INVENTION

The present invention relates to an optical waveguide sensor which incorporates an appropriate indicator sensitive to the analyte under investigation and retains said indicator within the optical waveguide in a unique fashion in one or more preformed cells. The invention is suitable for absorption, fluorescent, luminescent and other indicators which may be contained in the cells.

Typically, the waveguide will be an optical fiber; but the invention is equally applicable to any other form of waveguide which may be processed to incorporate indicator-containing cells. Thus, the waveguide may be an integrated optic chip, for example a slab of material, such as lithium niobate, in which an appropriate optical circuit may be photo lithographically printed. Still other forms of waveguide, provided they are capable of being processed in the manner herein described, may be used to form sensors according to the invention. However, the preferred waveguides are optical fibers, and the invention will be particularly described hereinafter with reference to this preferred embodiment.

The use of optical fibers in sensors or probes is known in the art and in such sensors the fiber operates as means for transmitting electromagnetic radiation from a source to a medium containing an analyte and returning a signal to a suitable detector. In an absorption system the return signal is a beam whose intensity is attenuated by absorption by the indicator, the amount of absorption being dependent upon the concentration of the analyte which alters the absorption characteristics of the indicator. In a fluorescent or luminescent system the return signal is a fluorescent or luminescent emission, the intensity of which is dependent upon the concentration of the analyte.

Examples of absorption indicators for pH determination are:
  phenol red, cresol red, bromothymol blue and metacresol purple.

If used in conjunction with bicarbonate ions, each of these indicators may be used to determine carbon dioxide. Phenol red is a preferred absorption indicator.

Examples of fluorescent indicators are:
β-umbelliferone for pH or pCO$_2$, pyrene butyric acid for pO$_2$.

Other determinations may be performed with appropriate indicators.

In a preferred absorption system comprising a single optical fiber the indicator is usually located at or near the distal end of the fiber and the distal end is provided with a reflective surface for the return signal. The reflective surface may be a metal disc bonded to the distal end of the fiber with a suitable adhesive, for example, an epoxy resin, or a layer of metal particles, metal flakes or reflective white particles. The particles are suspended in an appropriate medium, such as a liquid epoxy resin, the end of the fiber is dipped into the suspension, whereby the suspension adheres to the end when it is withdrawn and the epoxy is allowed to cure or set so that a layer of the particles is deposited on the end of the fiber. The advantage of this procedure over the bonding of a metal disc is that it is simple and a microscope is not required for the placement of the reflective surface. A preferred material for the reflective white particles is titanium dioxide or barium sulphate.

DESCRIPTION OF THE DRAWINGS

A preferred embodiment of the invention is illustrated in the accompanying drawings, in which.

Figure 1:
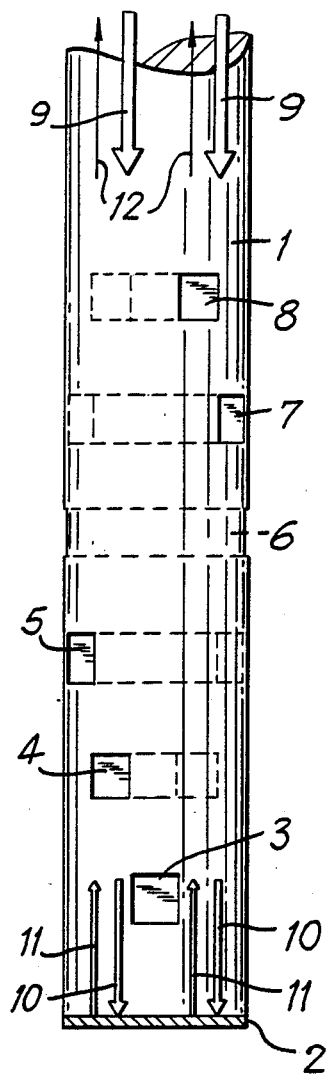
FIG. 1 is a side elevation of an optical fiber containing cells in accordance with the invention.
Figure 2:
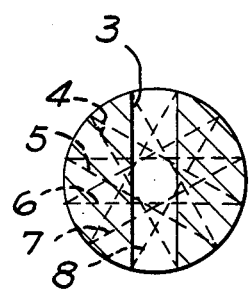
FIG. 2 is a cross section of the optical fiber of FIG. 1.
Figure 3:
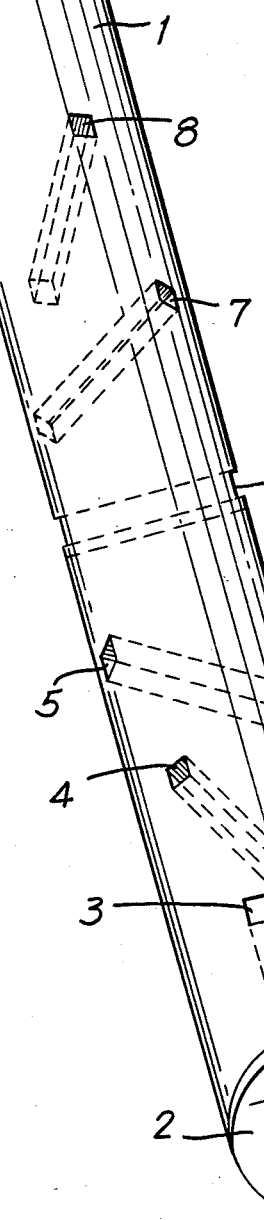
FIG. 3 is a schematic perspective view of the optical fiber showing a helical disposition of the cells.

The embodiment illustrated in FIGS. 1, 2 and 3 of the drawing comprises an optical fiber 1 having a distal end with a reflective surface 2. The reflective surface is formed by a layer of reflective white particles of, for example, titanium dioxide or barium sulphate suspended in an epoxy resin. The curing of the resin forms a stable bond to the end of the fiber.

The optical fiber is made from a suitable material for transmitting electromagnetic radiation; such as fused silica or an acrylic polymer, particularly polymethyl methacrylate. Typically, the fiber will have a diameter of 125 to 250 microns.

A series of cells 3, 4, 5, 6, 7, 8 is located in the fiber along a portion near to, but set back from, the distal end. These cells are formed by ablating holes in the fiber to form an array which substantially covers the cross-sectional area of the fiber as shown in plan in FIG. 2. A preferred arrangement to achieve the desired substantial coverage is a helical array as shown in perspective in FIG. 3. The desirability of an arrangement which provides substantial coverage over the cross-sectional area of the fiber is that such arrangement ensures that incident radiation transmitted from a source (not shown) to the distal end of the fiber and return reflected radiation pass through at least one indicator-containing cell and thereby provide an appropriate signal for determination of the analyte under investigation.

It is to be understood that the helical array illustrated in FIG. 3 is not essential to provide the pattern illustrated in FIG. 2 since the directional sequence of the cells may be altered and still produce the same coverage. Furthermore, although in the illustrated embodiment the cells extend diametrically through the fiber, the desired coverage may be achieved with holes which do not extend through the full diameter of the fiber.

In the embodiment illustrated in the drawings each of the cells 3-8 is of square cross-section. However, any convenient cross-section may be chosen. The configuration of said cross-section may be determined by the shape of the mask through which the laser radiation is transmitted. The cells are preferably formed by ablating the fiber with high energy radiation from a suitable laser, preferably an excimer laser.

In a fiber having a cross-sectional diameter of 125 to 250 microns the cells will usually be about 50 to 100 microns square respectively and the cells will be separated from each other by a distance of about 300 to 500 microns. Although not drawn exactly to scale, the disposition of the cells with respect to each other and to the distal end of the fiber is illustrated in FIG. 1.

In preparing the sensor, the portion of the fiber containing the cells is immersed in a solution of a suitable indicator. The assembly containing the solution and the fiber is then placed in a vacuum chamber wherein it is subjected to a vacuum so that the cells are evacuated. Preferably the solution includes ingredients capable of forming a gel or other suitable solid phase adapted to be cured or otherwise set so that the indicator is retained in the cells in a stable manner. An example of a suitable indicator-containing composition is illustrated hereinafter. Preferably the refractive index of the indicator-containing gel should be matched to the refractive index of the optical fiber material.

When the indicator-containing gel or solid is retained in the cells the sensor is complete. In operating the sensor the portion of the optical fiber with the indicator-containing cells is immersed in a liquid medium containing the analyte under investigation.

Source radiation of a suitable wavelength is transmitted along the fiber toward the distal end 2. The incident radiation is represented by arrows 9 in FIG. 1. The incident radiation passes through the indicator-containing cells, wherein some of its energy is absorbed, and reaches the reflective surface 2 as represented by arrows 10. The radiation reaching the reflective surface is reflected as represented by arrows 11 and the reflected signal passes again through the cells wherein energy is again absorbed and returns along the fiber, as represented by arrows 12, to a detector (not shown) where the signal is analyzed and the relative intensity gives a determination of the analyte. The difference in thickness of the arrows 9, 10, 11 and 12 (not to scale) is intended to give a visual indication of the diminution of intensity between the incident radiation and the return signal.

As described above, the cells are preferably formed by ablating the optical fiber with a high energy laser. Ablation is a term of art meaning to remove material from a solid, for example by cutting, melting or vaporization, and is used herein to mean the formation of holes without debris, for example by drilling or boring with laser radiation or other suitable drilling means.

The ablation is preferably conducted by directing a beam of high energy electromagnetic radiation, preferably from an excimer laser, against a chosen point in the selected portion of the optical fiber for a time sufficient to form a hole or cell of the desired depth. Using an excimer laser, which provides pulsed radiation, the time required to form the desired cell depends upon the nature and dimensions of the fiber and the energy of the laser radiation. For example, using laser radiation at a pulse rate of about 50 to 100. Hertz at an energy density of about 5 to 20 joules/sq. cm. the time to ablate holes through a 250 diameter polymeric optical fiber is about 5 to 10 seconds. In the preferred embodiment described herein the hole extends through the whole width of the fiber.

The array of cells illustrated in FIGS. 1 to 3 may be produced by at least two procedures.

The first procedure comprises ablating a first cell, for example the cell nearest the distal end of the fiber, moving the fiber longitudinally while turning it through an angle of 30°, ablating a second cell and repeating the moving, turning and ablating procedure until the desired number of cells, in this instance six, is formed. This procedure requires a separate period of laser radiation for the formation of each hole or cell and means for synchronizing the moving, turning and ablating steps.

In a second procedure the desired array of cells is formed without moving the fiber, but by using a multiple-hole drilling rig whereby beams of radiation from a single laser are directed through a series of reflectors located around the portion of the fiber to be ablated. The location of each reflector determines the site of ablation for each cell in the desired array The reflector is preferably a mirror or a prism.

The following Example illustrates a preferred embodiment of the invention with reference to the materials used and the manner in which the invention is performed.

EXAMPLE

An optical fiber having a diameter of 0.010 inches (250 microns) and made from polymethyl methacrylate with a fluorinated polymer cladding was used to prepare a sensor according to the invention.

To prepare the sensor, a series of six cells, each 100 microns square was ablated through the fiber using an excimer laser. Each cell passed along a fiber diameter, and was rotated about 30° with respect to each adjacent cell. The longitudinal spacing between the cells was about 300 to 500 microns. The resulting helical array ensured that radiation transmitted through the fiber would have to traverse at least one cell.

The distal end of the fiber, a short distance from the last cell, was cut square with a cutting blade and a reflective surface was bonded thereto. An optical connector was attached to the proximal end of the fiber (the fiber length being up to six feet).

An indicator solution was then prepared. The solution contained 0.6 grams of a powdered mixture comprising 73% acrylamide, 14% N,N-methylene-bis acrylamide and 12% ammonium persulfate by weight, and 1.4 ml. of a 300 millimolar phosphate buffer adjusted to pH 7.80 and saturated with phenol red.

The portion of the fiber with the six cells was then immersed in the above indicator solution and subjected to a vacuum to remove air from the cells. Several drops of N,N,N',N'-tetramethylenediamine was added to the solution. Within a few minutes the liquid converted to a solid gel. The optical fiber was removed from the gel and placed in a pH 7.30 buffer. Inspection of the fiber revealed that the cells were now filled with gel and that, within the gel, a significant amount of phenol red was permanently immobilized.

The fiber (now a pH sensor) was attached to a modified Cardiomet 4000 ® monitor (Biomedical Sensors Limited). The monitor provided an appropriate light source (green and red light emitting diodes (LED)), detector (photodiode) and software to calibrate the sensor and then to use the sensor to measure the pH of unknown solutions.

With the modified Cardiomet 4000 ® monitor the sensor was accurately calibrated using three pH standards. ($pH_1$, about 6.69; $pH_2$ about 7.29; $pH_3$ about 7.80 at room temperature). Calibration of the sensor was carried out according to the instructions provided with the monitor, i.e. in the known manner for the Cardiomet 4000 ® monitor.

After the initial calibration the sensor was left running for four days. At the end of this time no significant drift in the sensor was observed. (The resolution of the monitor is ±0.01 units). The response time of the sensor (0 to 90%) was about one minute.

We claim:

1. An optical waveguide sensor for determining an analyte in a medium, which sensor comprises an optical waveguide having a portion to be brought into contact with said medium, said portion having a plurality cells arranged in an aray which substantially covers the cross-sectional area containing an indicator sensitive to said analyte.

2. A sensor according to claim 1, in which the waveguide is an optical fiber.

3. A sensor according to claim 2, in which each of said cells is formed by ablating a hole in the optical fiber.

4. A sensor according to claim 3, in which said cell is ablated with a high energy laser.

5. A sensor according to claim 1, in which said array is a helical array.

6. A sensor according to claim 1, in which the analyte is the pH of the medium and the indicator is a pH-sensitive absorption indicator.

7. A sensor according to claim 6, in which the indicator is phenol red which is deposited in each cell in a gel.

8. A sensor according to claim 1, in which the waveguide is an optical fiber having a distal end and a reflective surface is bonded to said distal end.

9. A sensor according to claim 8, in which said reflective surface is a metal or a layer of reflective particles suspended in an epoxy resin.

10. A sensor according to claim 1, in which the optical fiber is made from polymethyl methacrylate.

11. A method for the preparation of an optical waveguide sensor for determining an analyte in a medium, which comprises selecting a portion of said waveguide, subjecting said portion to means for forming one or more cells within the waveguide, immersing said portion in a medium containing an indicator sensitive to said analyte and evacuating said one or more cells until each of said cells is filled with said indicator.

12. A method according to claim 11, in which said waveguide is an optical fiber.

13. A method according to claim 12, in which each of said cells is formed by ablating a hole in the optical fiber.

14. A method according to claim 13, in which said cell is ablated with a high energy laser.

15. A method according to claim 14, in which a plurality of cells is ablated in the optical fiber by ablating a first cell, then longitudinally moving and rotating the fiber and ablating a second cell and repeating the moving, rotating and ablating steps until the desired number of cells is formed, said cells being arranged in an array which substantially covers the cross-sectional area of the fiber.

16. A method according to claim 15, in which said array is a helical array.

17. A method according to claim 14, in which a plurality of cells arranged in an array which substantially covers the cross-sectional area of the fiber is ablated along said portion of the fiber by subjecting said portion to beams of radiation from a single laser wherein said beams are reflected by a series of reflectors, each of which is located around said portion at an angle which reflects its associated beam into said fiber at a site preselected to provide the relevant cell in the desired array.

18. A method according to claim 17, in which said array is a helical array.

19. A method for the preparation of an optical fiber pH sensor which comprises ablating a plurality of holes with an excimer laser to form cells in an array along a portion of an optical fiber, immersing said portion in a gel-forming solution of phenol red indicator and evacuating said cells so that the cells are filled with solution, removing the fiber from the solution and allowing an indicator-containing gel to form in each cell.

20. A method according to claim 19, in which a cross-linking agent is added to the solution to facilitate formation of said gel.

21. A method according to claim 19, in which said optical fiber has a distal end and a reflective surface is bonded to said distal end prior to or after said ablation step.

22. A method according to claim 21, in which said reflective surface is formed by suspending reflective particles in a liquid adhesive, immersing the distal end of said optical fiber in said liquid suspension, withdrawing said distal end from said liquid and curing said adhesive to provide a layer of said reflective particles on said distal end of the fiber.

* * * * *

UNITED STATES PATENT AND TRADEMARK OFFICE
CERTIFICATE OF CORRECTION

PATENT NO. : 4,889,407
DATED : Dec. 26, 1989
INVENTOR(S) : David R. Markle, Barry C. Crane, Michael P. Irvine It is certified that error appears in the above-identified patent and that said Letters Patent is hereby corrected as shown below:

Column 3, line 2: change "7/8-umbelliferone" to -- $\beta$-umbelliferone --

Column 6, (in claim 1) line 20: change "aray" to -- array --

Line 21: - after "area" insert -- of the waveguide, each of said cells --

Signed and Sealed this

Sixth Day of November, 1990

Attest:

HARRY F. MANBECK, JR.

*Attesting Officer*     *Commissioner of Patents and Trademarks*